(12) United States Patent
Blacklin (10) Patent No.: US 8,667,659 B2
(45) Date of Patent: Mar. 11, 2014

(54) SYSTEM AND METHOD FOR COUPLING AN EXTENDABLE ELEMENT TO AN ACTUATOR

(75) Inventor: Peter Alfred Blacklin, Columbia, MD (US)

(73) Assignee: Mettler-Toledo AG, Greifensee (CH)

( * ) Notice: Subject to any disclaimer, the term of this patent is extended or adjusted under 35 U.S.C. 154(b) by 654 days.

(21) Appl. No.: 13/009,283

(22) Filed: Jan. 19, 2011

(65) Prior Publication Data

US 2012/0180290 A1   Jul. 19, 2012

(51) Int. Cl.
*B21D 39/03* (2006.01)

(52) U.S. Cl.
USPC .................. 29/428; 29/700; 29/434; 29/252; 29/255; 29/278; 29/270; 29/506; 73/864.73; 254/134.3 FT; 254/134.3 R (58) Field of Classification Search
USPC ........... 29/428, 700, 728, 434, 443, 469, 506, 29/252, 270, 278, 255; 73/864, 864.13, 73/864.51, 864.73
See application file for complete search history.

(56) References Cited

U.S. PATENT DOCUMENTS

| | | | | |
|---|---|---|---|---|
| 5,024,110 A | * | 6/1991 | Doussiet et al. | 73/864.62 |
| 5,156,160 A | * | 10/1992 | Bennett | 600/567 |
| 5,249,583 A | * | 10/1993 | Mallaby | 600/567 |
| 5,349,875 A | * | 9/1994 | Sher et al. | 73/864.65 |
| 5,404,760 A | * | 4/1995 | Robinson et al. | 73/863.11 |
| 5,411,087 A | * | 5/1995 | Taylor | 166/264 |
| 5,566,576 A | * | 10/1996 | Sher et al. | 73/864.65 |
| 5,709,697 A | * | 1/1998 | Ratcliff et al. | 606/180 |
| 5,806,164 A | * | 9/1998 | Wilks | 29/426.5 |
| 5,889,217 A | * | 3/1999 | Rossabi et al. | 73/864.74 |
| 6,043,842 A | * | 3/2000 | Tomasch et al. | 348/164 |
| 6,065,355 A | * | 5/2000 | Schultz | 73/864 |
| 6,165,136 A | * | 12/2000 | Nishtala | 600/564 |
| 6,182,753 B1 | * | 2/2001 | Schultz | 166/162 |
| 6,182,757 B1 | * | 2/2001 | Schultz | 166/264 |
| 6,189,392 B1 | * | 2/2001 | Schultz | 73/864 |
| 6,192,984 B1 | * | 2/2001 | Schultz | 166/264 |
| 6,193,673 B1 | * | 2/2001 | Viola et al. | 600/568 |
| 6,554,779 B2 | * | 4/2003 | Viola et al. | 600/568 |

(Continued)

FOREIGN PATENT DOCUMENTS

| | | |
|---|---|---|
| CN | 201166619 Y | 12/2008 |
| DE | 20103617 U1 | 5/2001 |
| DE | 202004015643 U1 | 1/2005 |
| DE | 102009011973 A1 | 9/2010 |

*Primary Examiner* — Jermie Cozart
*Assistant Examiner* — Bayan Salone
(74) *Attorney, Agent, or Firm* — Standley Law Group LLP (57) ABSTRACT

A system and method for releasably coupling an extendable element to an actuator. Such a system may include an actuator housing with a specially adapted integral connecting end having a cavity therein. An extendable element may extend into the cavity through an opening in the connecting end of the housing and be coupled to a motive element of the actuator by a rotatable collar that resides in the cavity. A cover plate forms a part of the actuator housing connecting end. The cover plate compliments the integral portion of the connecting end and, in conjunction therewith, encloses the collar and the coupled portion of the extendable element. A substantially hollow end cap is passed over the extendable element and releasably attached to the actuator housing to enclose the distal connecting end thereof. In some embodiments, the coupled extendable element may reciprocate within an outer tube that is also releasably attached to the actuator housing.

20 Claims, 10 Drawing Sheets

(56) References Cited

U.S. PATENT DOCUMENTS

| | | | |
|---|---|---|---|
| 6,561,046 B1 * | 5/2003 | Taylor et al. | 73/863.23 |
| 6,918,310 B2 * | 7/2005 | Bjork et al. | 73/863.81 |
| 7,030,403 B2 * | 4/2006 | Feldsine et al. | 250/573 |
| 7,039,994 B2 * | 5/2006 | Crawford | 29/252 |
| 7,160,511 B2 * | 1/2007 | Takahashi et al. | 422/504 |
| 7,165,305 B2 * | 1/2007 | Kenney et al. | 29/434 |
| 7,276,032 B2 * | 10/2007 | Hibner | 600/564 |
| 7,472,615 B2 * | 1/2009 | Mayeaux | 73/866.5 |
| 7,600,580 B2 * | 10/2009 | Cravatte et al. | 175/20 |
| 7,617,745 B1 * | 11/2009 | Mayeaux | 73/866.5 |
| 7,703,344 B2 * | 4/2010 | MacPherson et al. | 73/864.73 |
| 7,753,857 B2 * | 7/2010 | Hibner | 600/566 |
| 7,758,515 B2 * | 7/2010 | Hibner | 600/566 |
| 7,858,038 B2 * | 12/2010 | Andreyko et al. | 606/144 |
| 7,867,173 B2 * | 1/2011 | Hibner et al. | 600/568 |
| 7,886,624 B1 * | 2/2011 | Mayeaux | 73/866.5 |
| 8,016,772 B2 * | 9/2011 | Heske et al. | 600/566 |
| 8,057,756 B2 * | 11/2011 | Londo et al. | 422/501 |
| 8,088,081 B2 * | 1/2012 | Field et al. | 600/567 |
| 8,096,199 B2 * | 1/2012 | Riazanskaia et al. | 73/864.33 |
| 8,312,780 B2 * | 11/2012 | Blacklin et al. | 73/863 |
| 8,365,617 B2 * | 2/2013 | Blacklin et al. | 73/863.51 |
| 8,429,986 B2 * | 4/2013 | Lee et al. | 73/864 |
| 8,522,629 B2 * | 9/2013 | Lee et al. | 73/864.35 |
| 2001/0011156 A1 * | 8/2001 | Viola et al. | 600/568 |
| 2003/0143752 A1 | 7/2003 | Feldsine et al. | |
| 2004/0019299 A1 * | 1/2004 | Ritchart et al. | 600/567 |
| 2004/0055402 A1 * | 3/2004 | Pensis et al. | 73/866.5 |
| 2006/0030785 A1 * | 2/2006 | Field et al. | 600/567 |
| 2006/0074345 A1 * | 4/2006 | Hibner | 600/566 |
| 2006/0074346 A1 * | 4/2006 | Hibner | 600/566 |
| 2007/0032741 A1 * | 2/2007 | Hibner et al. | 600/566 |
| 2007/0149894 A1 * | 6/2007 | Heske et al. | 600/566 |
| 2007/0255173 A1 * | 11/2007 | Hibner | 600/566 |
| 2008/0022753 A1 * | 1/2008 | MacPherson et al. | 73/31.01 |
| 2008/0190218 A1 * | 8/2008 | Riazanskaia et al. | 73/864 |
| 2009/0038419 A1 * | 2/2009 | Hiller et al. | 73/864.73 |
| 2011/0172676 A1 * | 7/2011 | Chen | 606/107 |
| 2011/0318243 A1 * | 12/2011 | Blacklin et al. | 422/509 |

* cited by examiner

SYSTEM AND METHOD FOR COUPLING AN EXTENDABLE ELEMENT TO AN ACTUATOR

TECHNICAL FIELD

The present invention is directed to an extendable element-to-actuator coupling system and method, such as a system and method for coupling an extendable sample capture element of a sampling device to an actuator.

BACKGROUND

As would be obvious to one of skill in the art, there are a number of devices wherein an extendable/retractable (i.e., actuated) element is coupled to an actuator that provides for the extension and retraction movement thereof. Where it is desired or necessary to periodically decouple such an element from the actuator to which it is coupled, it can also be understood that a coupling system that facilitates decoupling (and re-coupling) would be advantageous.

Various devices may benefit from such a coupling system. Without limitation, one such device is a sampling device like that shown and described in U.S. patent application Ser. No. 12/823,655, filed on Jun. 25, 2010. One embodiment of this sampling device includes a substantially cylindrical and hollow outer (probe) tube of some length having concentrically arranged therein and at a distal end thereof, an assembly including an outer sleeve, an inner sleeve and an extendable sample capture element. The sample capture element is located to reciprocate within the probe tube and, more specifically, within the inner sleeve. The sample capture element is provided with a sample capture pocket that, during sample capture element extension, is exposed to and captures an amount of a sample of interest.

During use of this probe, the sample capture element is extended into a material of interest to capture a sample thereof and then subsequently retracted back into the tube. Consequently, the sample capture element is coupled to an actuator adapted to produce its extension and retraction. At the desired time, the actuator is activated to extend the sample capture element into and to subsequently withdraw the sample capture element from a material of interest, as described above.

As mentioned above, it may be desirable or necessary to decouple an actuated element from an actuator. This may be true for various reasons, many of which may depend on the design and construction of the device that incorporates the actuated element and/or on the nature of its use. In the case of the aforementioned sampling probe, decoupling of the actuator from the sample capture element and associated tube may be desirable, for example, to permit changing of the outer sleeve and/or to change the tubing that transfers material to and from the sample capture element. It may also be desirable to decouple an extendable portion of the sampling probe from the actuator simply for purposes of maintenance or cleaning. In any event, the probe coupling system and method of the present invention facilitates such decoupling and re-coupling.

SUMMARY OF THE GENERAL INVENTIVE CONCEPT

Embodiments of the present invention provide for secure retention (coupling) of an extendable (e.g., reciprocatable) element to an actuator, while simultaneously allowing for quick and simple removal therefrom and reinstallation of the extendable element thereto. Embodiments of the present invention may be employed to couple a wide variety of extendable elements and associated actuators that may be used in a number of different fields for a number of different purposes.

In the case of an exemplary sampling probe, as discussed above, an actuator (e.g., pneumatic or hydraulic cylinder) may include an actuator housing having a distal connecting end that is adapted for attachment to a probe tube containing a reciprocal sample capture element. The actuator housing is adapted for attachment of the probe tube thereto, and also facilitates coupling of the reciprocal sample capture element to the actuator. More specifically, the connecting end of the actuator body is of split construction, such that a cover plate may be removed to expose a rotatable retention collar. The retention collar is coupled at one end to a retention collar receiver or other connecting element of the actuator, while the other end is adapted for coupling to the sample capture element.

A slot is located in the distal end of the actuator housing receiving section. A proximal (retained) end of the probe tube passes through the slot. A pair of grooves are cut into the exterior of the probe tube at a proper location to engage a mating pair of retention pins that protrude from the distal end of the actuator housing. The probe tube is thus prevented from being axially withdrawn from the actuator housing.

A proximal (retained) end of the sample capture element extends from the proximal end of the probe tube. The distal end of the rotatable retention collar also includes a receiving slot, which is cut into the retention collar so as to form a rib. The sample capture element is provided with a retention groove near its proximal end that is engaged by the rib in the retention collar when the probe tube/sample capture element is properly inserted into the actuator housing. The retention collar is then rotated (e.g., 180 degrees) within the actuator housing to provide for a secure coupling of the sample capture element to the actuator.

The cover plate is installed over the mating split portion of the actuator housing. The cover plate is internally configured to receive the retention collar and probe tube, and may also accept a portion of the retention pins that extend from the corresponding portion of the actuator housing. An end cap covers the connecting end of the actuator housing and is releasably affixed thereto by threaded engagement with threads located proximally of the actuator housing distal end. The end cap includes a central bore through which the probe tube passes. An opening may be formed through the actuator housing to permit the passage therethrough of material supply/return lines that are connected to a proximal end of the sample capture element. A like or similar arrangement may be used to releasably attach another type of extendible element to an actuator.

As will be more clearly understood from the following detailed description of exemplary embodiments, a coupling system of the present invention allows for a bi-directional force to be applied to an extendable element by an actuator coupled thereto. That is, the extendable element is coupled to the actuator in a manner that allows the actuator to both push and pull the extendable element.

Additionally, in embodiments where an extendable element is arranged within an outer tube, a coupling system of the present invention inherently produces a concentric arrangement of the extendable element in the outer tube. The secure coupling of the extendable element to an actuator by a system and method of the present invention further results in a secure fixed end condition that minimizes the effect of non-axial forces that might be applied to the extendable element (and outer tube when present) during use and, therefore, minimizes the buckling of long extendable elements (or outer tubes).

Embodiments of a coupling system of the present invention may also be adapted to prevent the rotation of certain related components (e.g., tubes, sample collection devices, etc.) during extension/retraction of an extendable element. A coupling system and method of the present invention produces all of the aforementioned functionality while simultaneously permitting a quick and easy coupling and decoupling of an extendable element to an actuator.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIGS. 3A-3H illustrate the process of coupling a reciprocatable sample capture element and its associated cover tube to an actuator assembly using an exemplary coupling system comprising the components depicted in FIG. 1, wherein:

DETAILED DESCRIPTION OF EXEMPLARY EMBODIMENT(S)

One exemplary embodiment of an extendable element coupling system 5 for coupling an extendable element to an actuator according to the present invention is depicted in FIGS. 1-3H, in association with an exemplary sample capture device 100. The sample capture device 100 can be observed in a disassembled and fully assembled state in FIG. 1 and FIG. 2, respectively. Briefly, the sample capture device includes an actuator 10 having a linearly displaceable retention collar receiver 20 or similar element (see FIG. 3B) that resides within an actuator housing 15 and is used to produced a desired reciprocation of an associated and extendable sample capture element 125. A majority of the sample capture element 125 is located within an outer probe tube 105. The coupling system 5 provides for a quick and secure attachment of the probe tube 105 to the actuator housing 15 and coupling of the sample capture element 125 to a motive element (e.g., retention collar receiver) 20 of the actuator 10.

In use, the actuator 10 of the sample capture device 5 may be activated to extend a distal end of the sample capture element 125 into a material of interest, whereby a material sample is captured in a sample pocket not shown) of the sample capture element, and whereafter the sample capture element is retracted back into the probe tube 105 by the actuator with the material sample trapped in the sample capture pocket. Thus, it can be understood that a simple system and method for decoupling of the sample capture element 125 from the actuator 10 would be desirable, for example, to allow for cleaning and/or repair thereof, or for the installation of a sample capture element having a different sample capture pocket size and/or arrangement.

While a sample capture device is shown and described herein in connection with describing the present invention, it is to be realized that the sample capture device is shown and described for purposes of illustration only, and coupling systems and methods of the present invention are not limited to use with this exemplary sample capture device, or to a sample capture device in general. Rather, it should be apparent to one of skill in the art that a coupling system and method of the present invention may also be used to couple extendable elements of various other devices to associated actuators.

Figure 1:
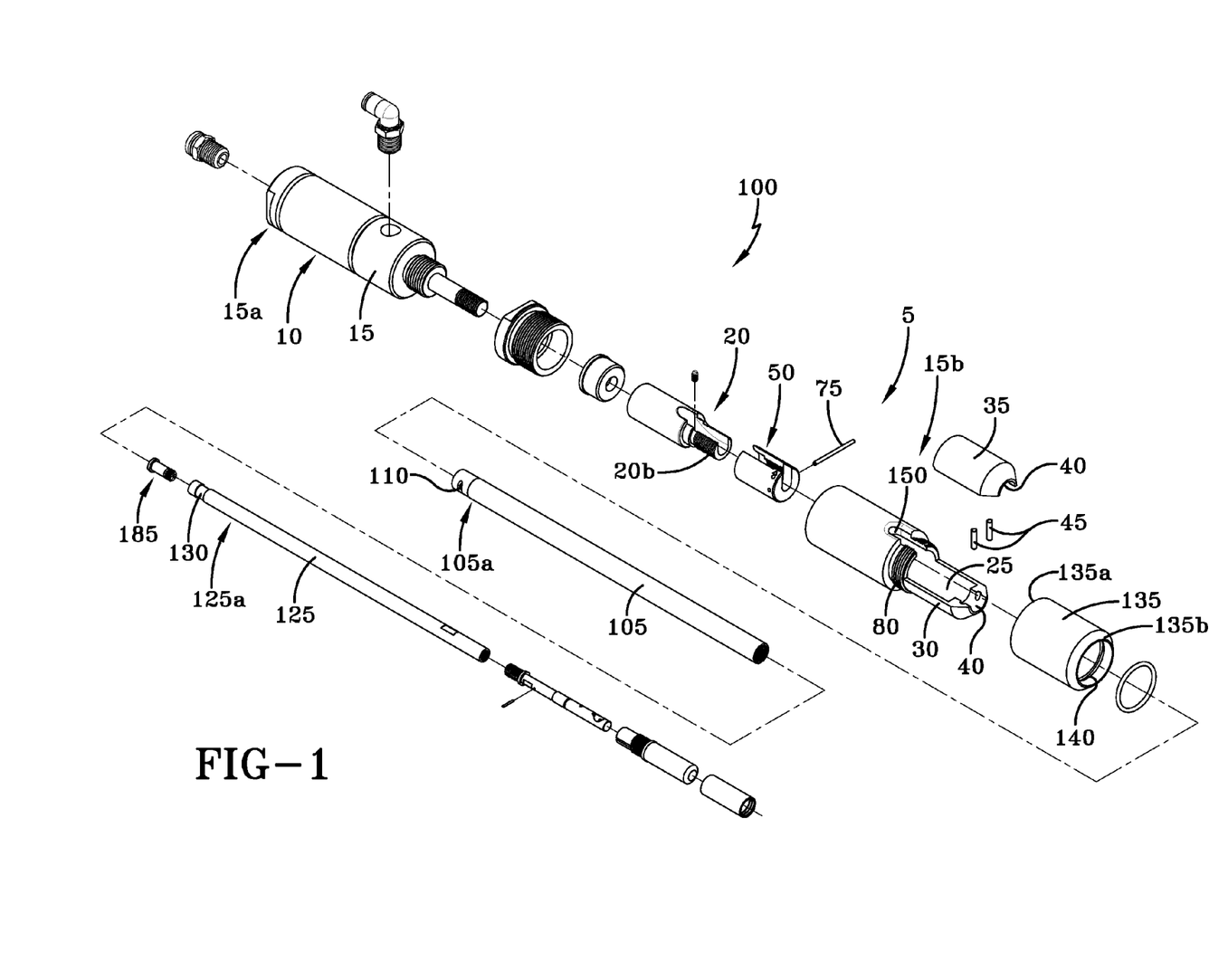
FIG. 1 is an exploded view of an exemplary sample capture device that employs an exemplary embodiment of a coupling system of the present invention.

Referring again to the disassembled view of FIG. 1, the exemplary sample capture device 100 provided for illustrating the present invention more specifically includes a substantially cylindrical linear actuator 10 having a housing 15 with a proximal end 15a and a distal connecting end 15b. The distal connecting end 15b of the actuator housing 15 is adapted for attachment of the sample capture device probe tube 105 thereto, and to facilitate coupling of the associated reciprocatable sample capture element 125 to the motive element (i.e., retention collar receiver) 20 of the actuator 10. More specifically, the connecting end 15b of the actuator housing 15 includes an internal cavity 25 that accommodates and surrounds various components of the exemplary extendable element attachment system 5 of the present invention.

The connecting end 15b of the actuator housing 15 is also of split construction—meaning that the actuator housing at the connecting end is divided along a plane that runs substantially parallel to its axial centerline. Termination of the actuator housing integral connecting end at this plane forms a cover plate mating face 85. Consequently, the connecting end includes an integral half 30 that is a unitary part of the housing, and a corresponding half that is provided as a removable cover plate 35 (see FIGS. 1 and 3E-3F) of the coupling system 5. The cover plate 35 mates with the cover plate mating face 85 of the actuator housing integral connecting end. The interior and exterior size and shape of the cover plate 35 preferably compliments the integral half 30 of the actuator housing connecting end 15b. That is, the interior and exterior size and shape of the cover plate 35 preferably accounts for the missing portions of the integral half 30 of the actuator housing connecting end 15b such that with the cover plate in place, a complete connecting end structure having a solid exterior and substantially hollow interior is created. In the particular example shown herein, the internal and external design, size and shape of the cover plate 35 is essentially a mirror image of the integral half 30 of the connecting end 15b of the actuator housing 15.

A portion of an axially centered slot 40 passes through the distal portion of each of the integral half 30 of the connecting end 15b of the actuator housing 15 and the corresponding cover plate 35, so as to permit passage of the sample capture device probe tube 105 and associated sample capture element 125 into the cavity 25 of the actuator housing 15. In other embodiments, the slot 40 may only permit access of an extendable element into the housing 15.

As can be best observed in FIGS. 1 and 3A-3C, a pair of probe tube retention pins 45 extends from the integral half 30 of the actuator housing connecting end 15b on either side of the hole 40 in this particular example. Therefore, the cover plate 35 includes corresponding apertures (not visible) that receive the protruding portion of the pins 45 when the cover plate is installed to the integral half 30 of the actuator housing connecting end 15b. Alternatively, the pins 45 may be installed in the cover plate 35 and apertures may be provided in the integral half 30 of the actuator housing connecting end 15b. It has been found, however, that placing the pins 45 in the integral half 30 of the actuator housing connecting end 15b facilitates installation of the sample capture device probe tube 105.

Figure 3A:
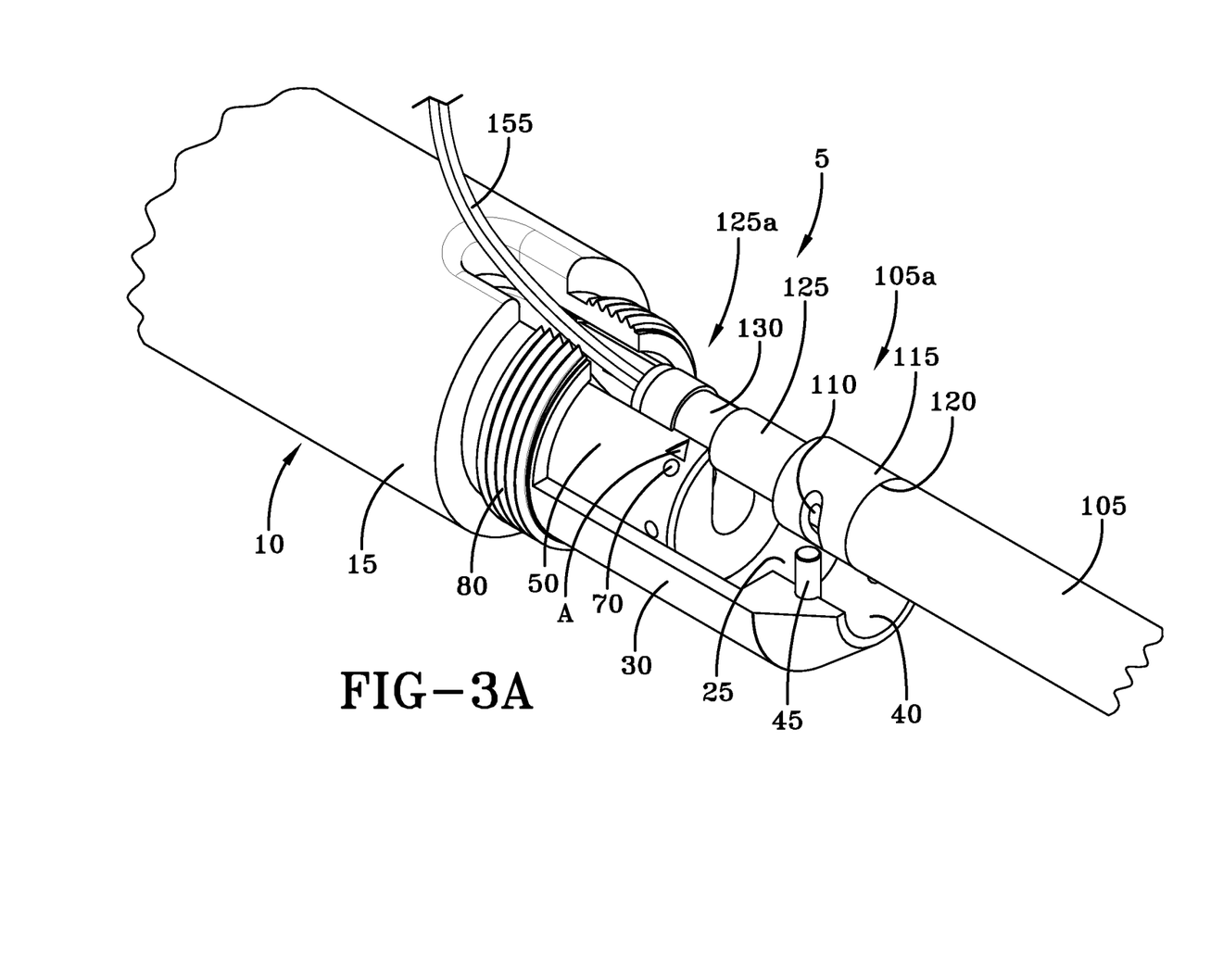
FIG. 3A is an enlarged view showing a distal connecting end of an actuator housing, with a sample capture device probe tube partially inserted therein.
Figure 3B:
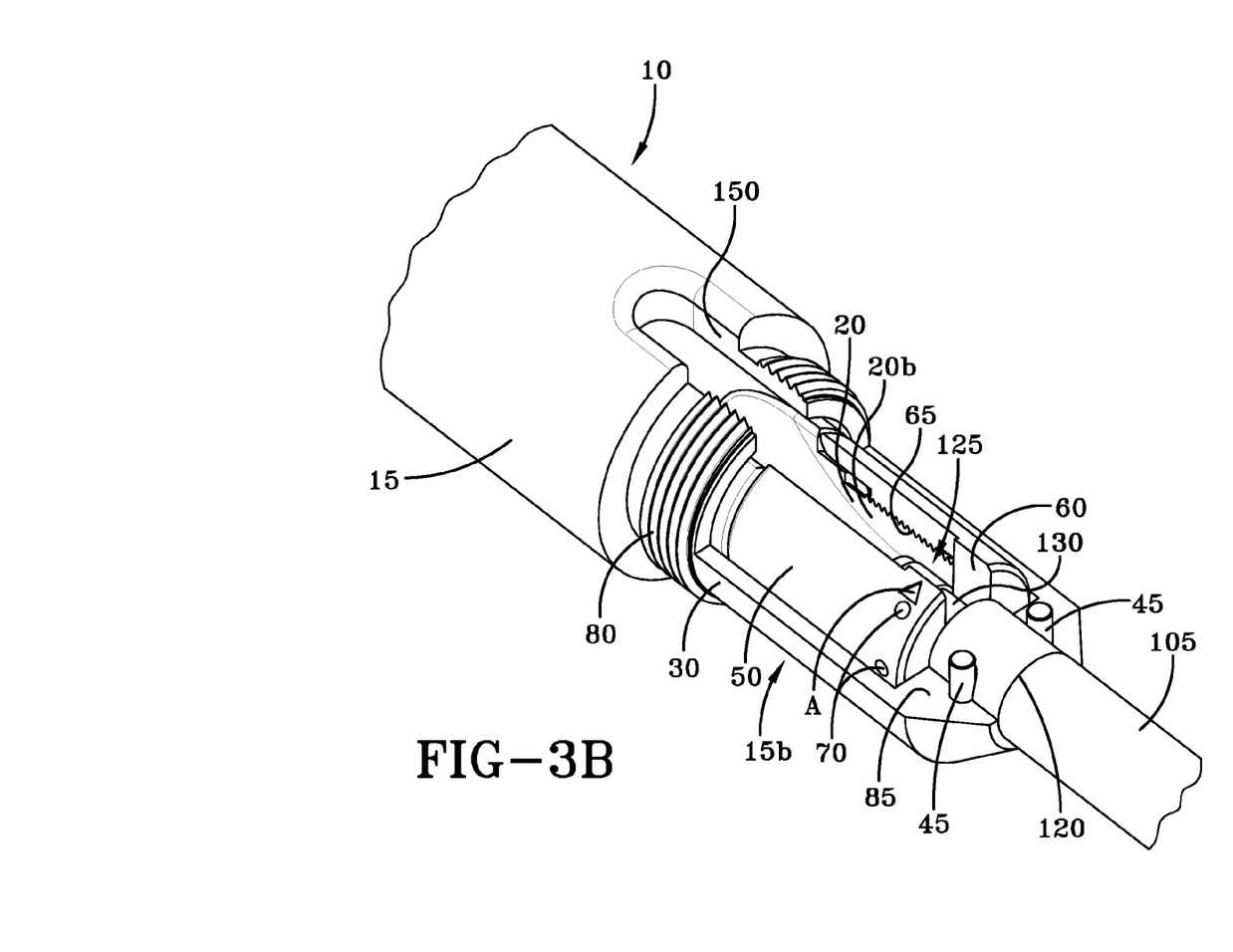
FIG. 3B shows the sample capture device probe tube fully inserted into the distal connecting end of the actuator housing.
Figure 3C:
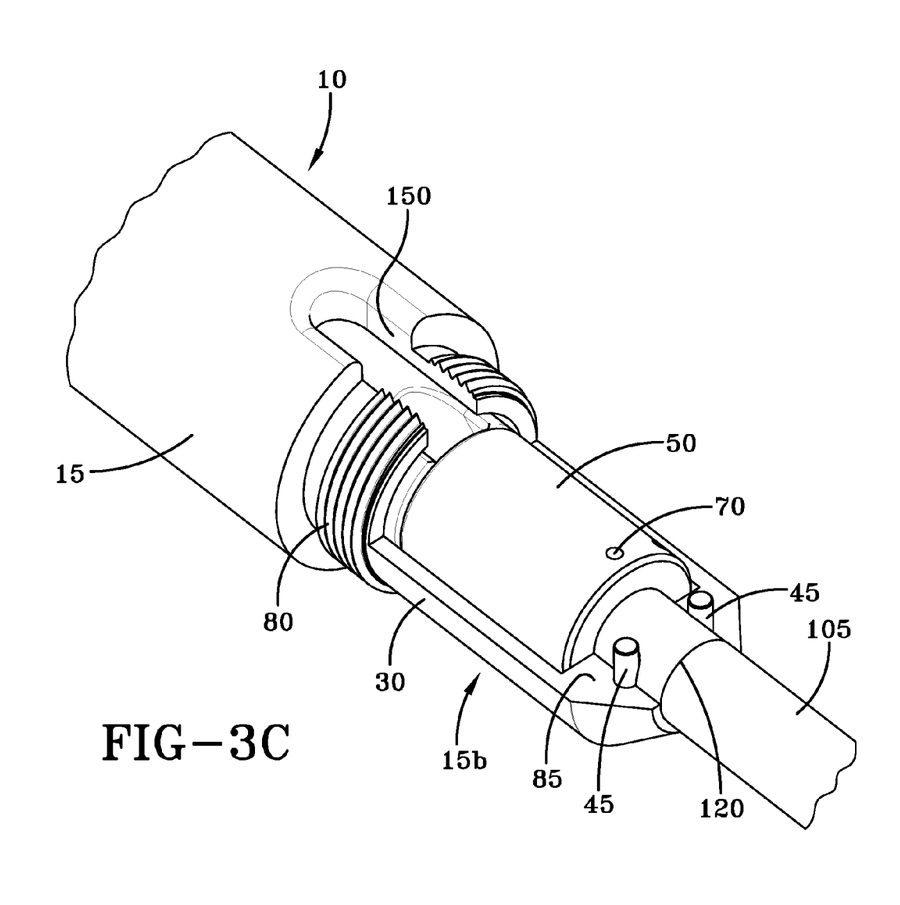
FIG. 3C again depicts the distal connecting end of the actuator housing, but with a rotatable retention collar engaged with a sample capture element that extends from the sample capture device probe tube.

A pair of diametrically-opposed and transversely-oriented retention grooves 110 (only one of which is visible) are cut into the exterior of the probe tube 105 near a proximal (retained) end 105a thereof and at a proper location to engage the pair of retention pins 45 that protrude from the connecting end 105a of the actuator housing 15. Thus, as shown in FIGS. 3B-3C, when the probe tube 105 is installed to the connecting end 15b of the actuator housing 15, engagement of the retaining pins 45 and the retention grooves 110 prevents the probe tube from being axially withdrawn from the actuator housing. The retained end 105a of the probe tube 105 may be optionally provided with an area of reduced diameter 115 for purposes of fit and function. As a result of this reduction in diameter, a shoulder 120 is formed on the probe tube. When present, the shoulder 120 may abut the distal end of the actuator housing connecting end 15b when the probe tube 105 is properly installed thereto.

As can be best observed in FIGS. 1 and 3A-3C, the sample capture element 125 of the sample capture device 100 extends from the retained end 105a of the probe tube 105. The sample capture element 125 is coupled to a retention collar receiver 20 of the actuator 10 (see FIGS. 3C-3D) to allow for both extension and retraction of the sample capture element as described above.

A rotatable retention collar 50 is provided to couple the sample capture element 125 to a retention collar receiver 20 of the actuator 10. The retention collar 50 is of substantially cylindrical shape and reciprocatably resides within the cavity section 25 of the actuator housing connecting end 15b. The retention collar 50 also includes a stepped sample capture element receiving slot 55 of a width designed to accommodate the sample capture element 125. The stepped design results in a retention rib 60 at the distal end of the retention collar. The sample capture element 125 includes a corresponding retention groove 130 near its proximal end 125a (see FIG. 3A) that is designed and located to engage the retention rib 60 of the retention collar 50 when the sample capture element is installed thereto.

Referring to FIGS. 3B-3C, it can be observed that once the proximal end 125a of the sample capture element 125 is properly installed into the sample capture element receiving slot 55 of the retention collar 50, the retention collar may be rotated about the retention collar receiver 20 and within the actuator housing connecting end cavity 25 to securely couple the sample capture element 125 to the retention collar receiver. In this example, the collar 50 may be rotated approximately 180 degrees, but the degree of collar rotation may vary in other embodiments. When the retention collar 50 is rotated over the sample capture element 125 as shown, engagement of the retention rib 60 and the groove 130 securely couples the sample capture element to the retention collar receiver 20 of the actuator such that the actuator can exert a bi-directional force on (i.e., can both extend and retract) the sample capture element.

Rotation of the retention collar 50 may be facilitated by the provision of one or more rotation tool holes 70 along the retention collar exterior circumference. Retention collar rotation may then be easily accomplished by inserting a collar rotation pin 75 (see FIG. 1) or a similar tool into a rotation tool hole 70 and subsequently turning (clockwise in this example) the retention collar 50 to lock the sample capture element 125 to the retention collar receiver 20.

As shown, the retention collar receiver 20 includes an externally-threaded section 20b. The retention collar 50 is provided with a corresponding internally-threaded section 65 that produces a threaded engagement of the retention collar and the retention collar receiver 20. Thus, the retention collar 50 is connected to, rotates around and reciprocates along with the retention collar receiver 20 within the cavity 25 of the actuator housing connecting end 15b. The sample capture element 125 may therefore be reciprocated within (extended from/retracted into) the probe tube 105 by actuator movement of the retention collar receiver 20.

As should also be apparent, rotation of the retention collar 50 (in the direction of the arrow A in this embodiment) also causes the retention collar to move linearly along the length of the retention collar receiver 20 and toward the proximal end 15a of the housing 15. This results in the retention grooves 110 of the probe tube being pulled securely against the retention pins 45 and, possibly, in the shoulder 120 (when present) of the probe tube 105 being pulled tightly against the distal face of the actuator housing connecting end 15b. The probe tube 105 is thus securely coupled to the actuator housing connecting end 15b.

Figure 3D:
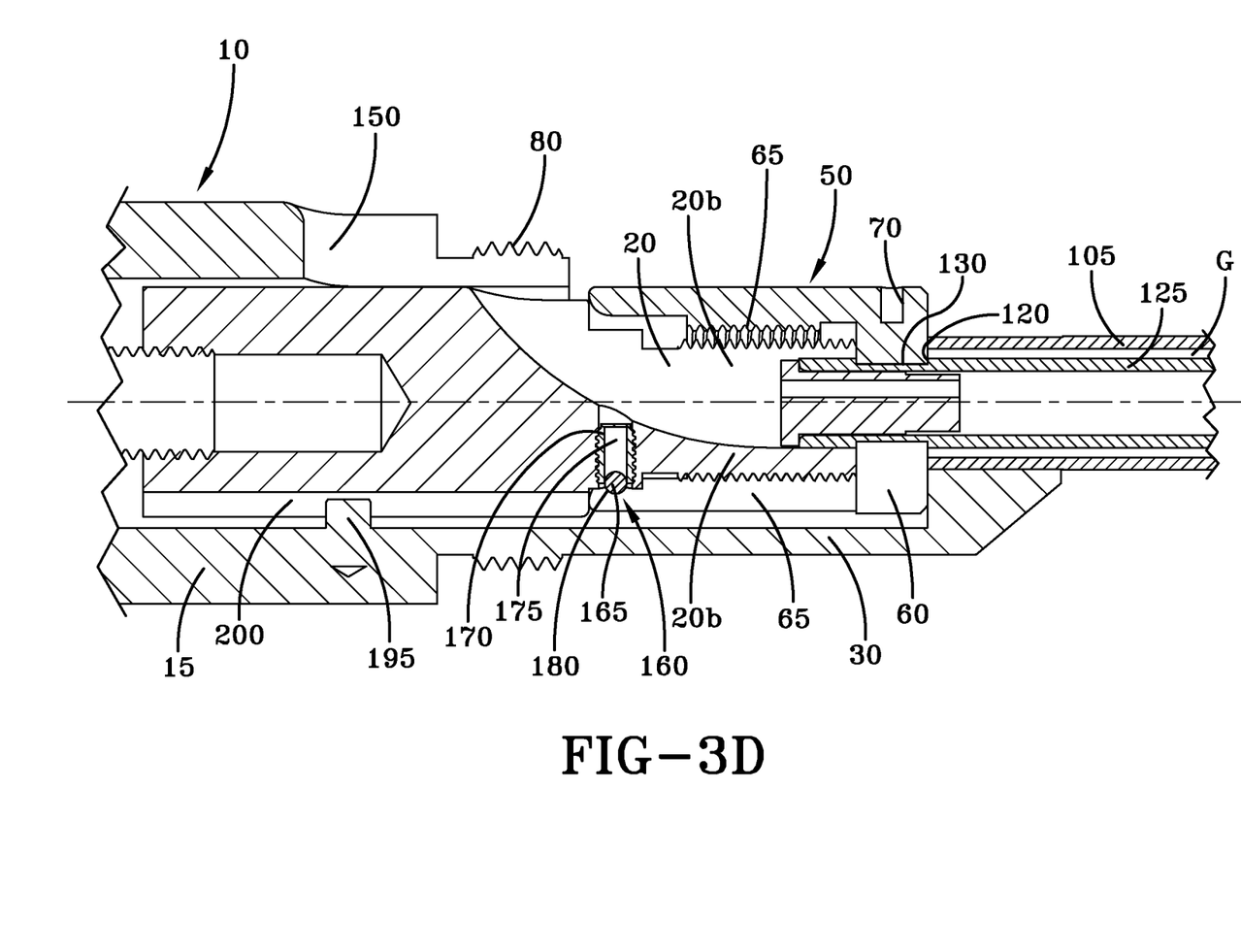
FIG. 3D is a side, cross-sectional view of the arrangement shown in FIG. 3C.
Figure 3E:
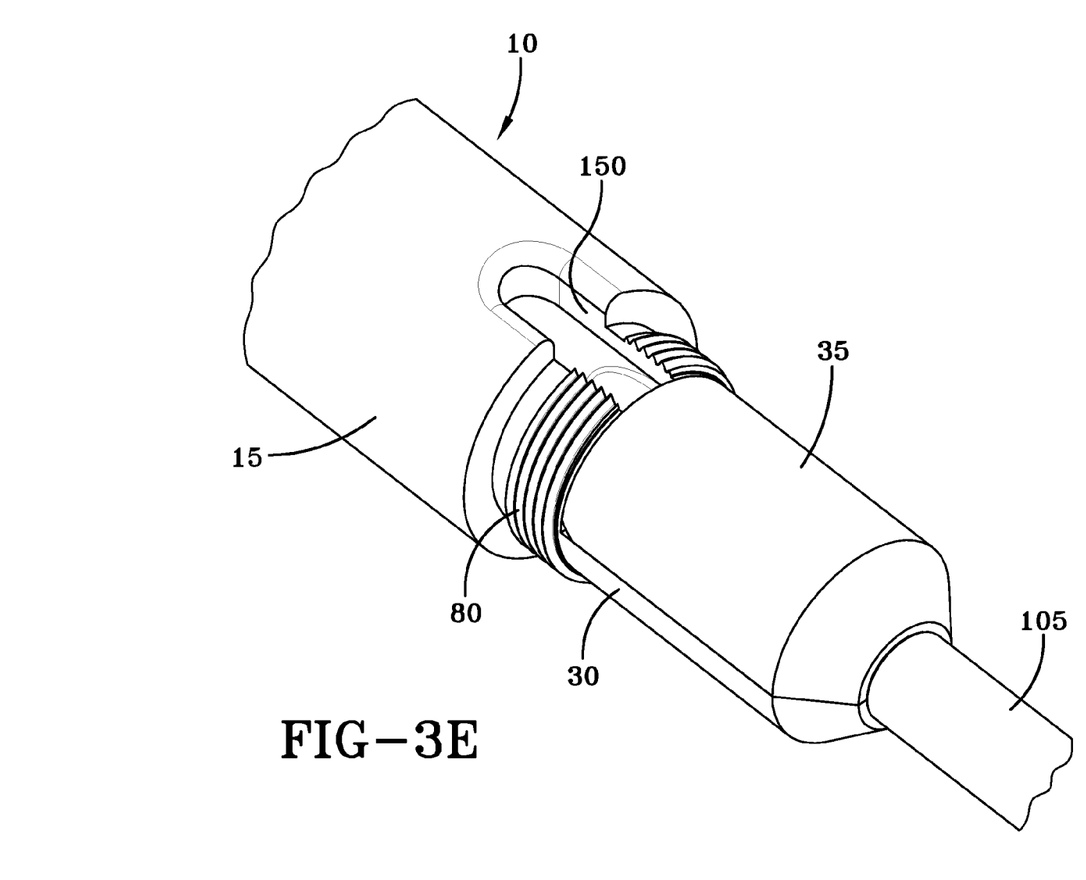
FIG. 3E illustrates the arrangement of FIG. 3C with a cover plate installed.
Figure 3F:
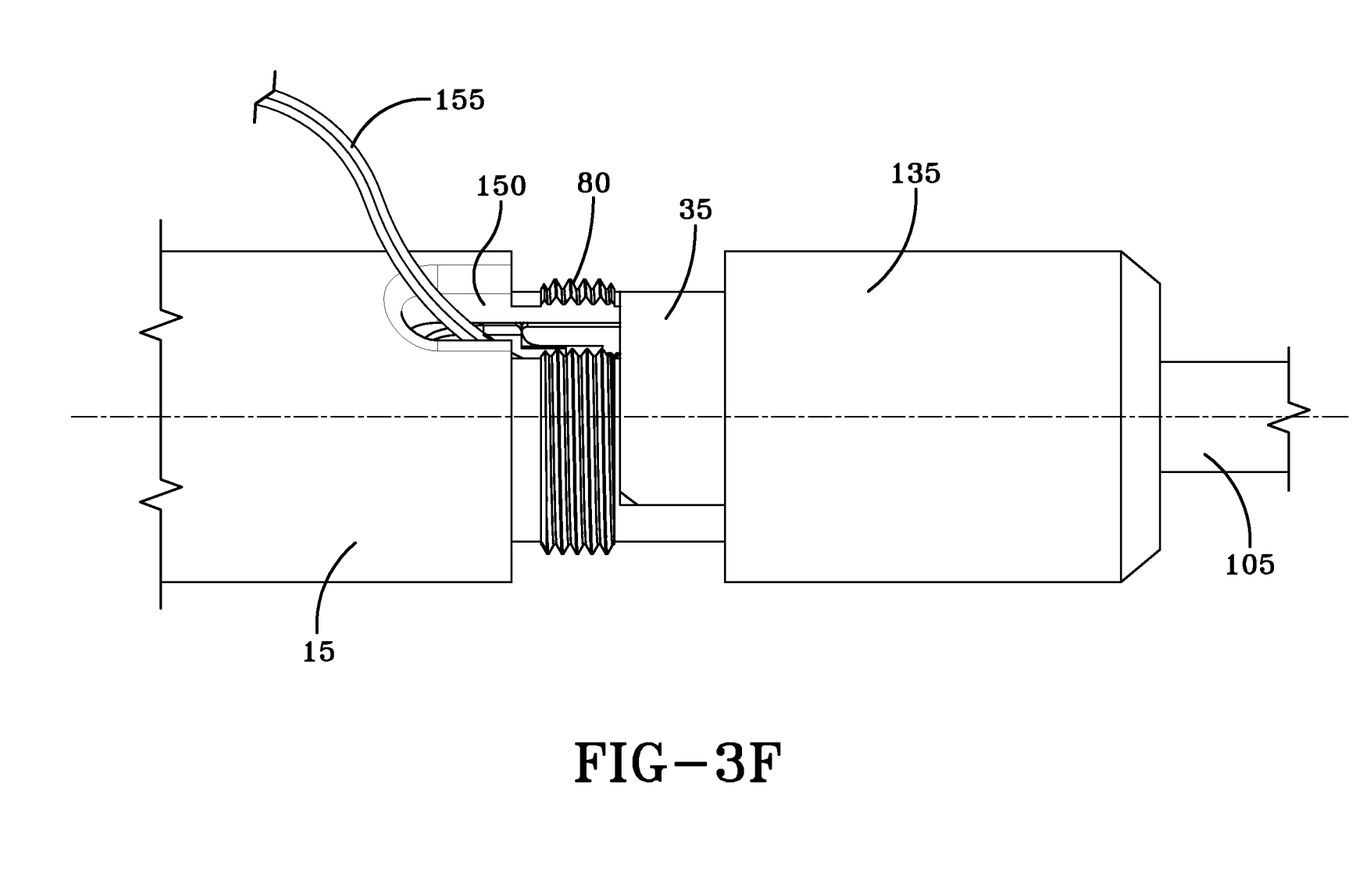
FIG. 3F depicts an end cap being installed over the arrangement of FIG. 3E.
Figure 3G:
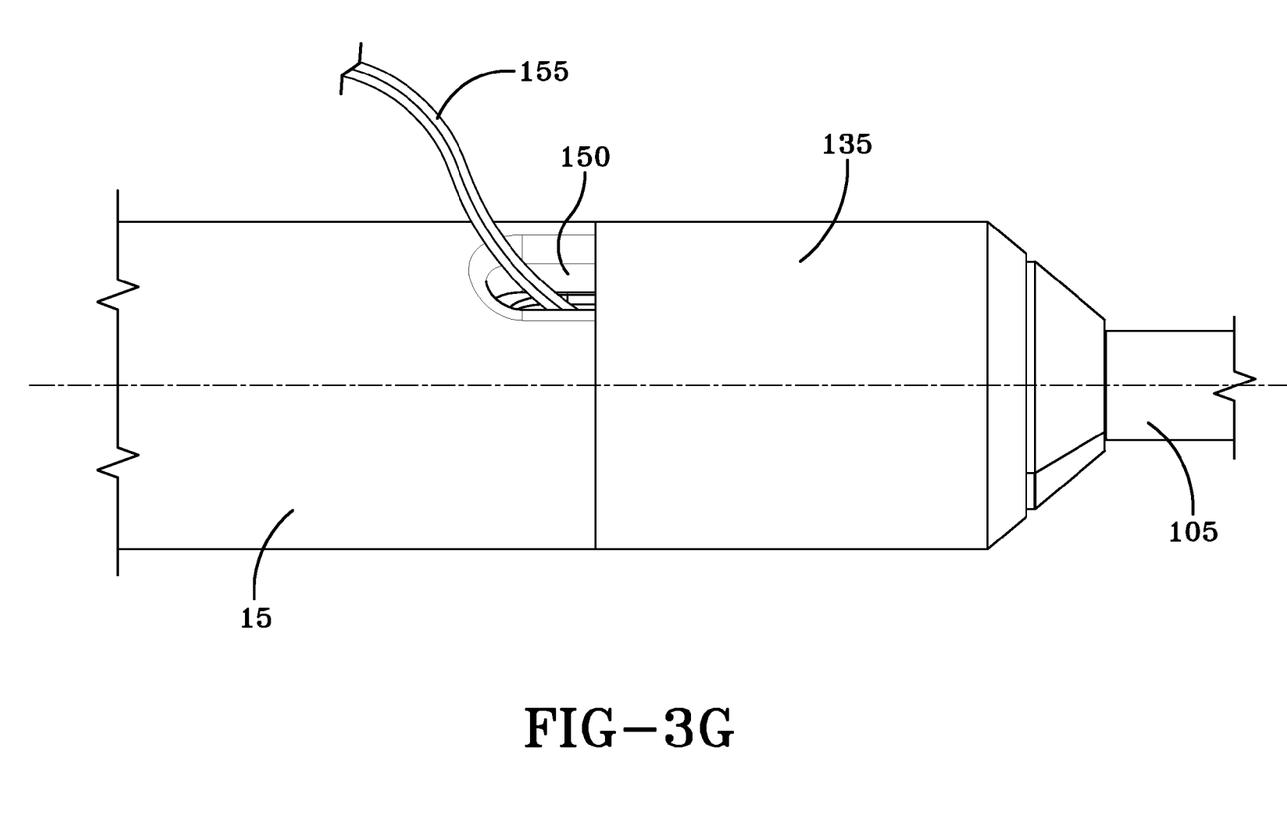
FIG. 3G shows the end cap in full threaded engagement with a corresponding threaded portion of the actuator housing distal connecting end.
Figure 3H:
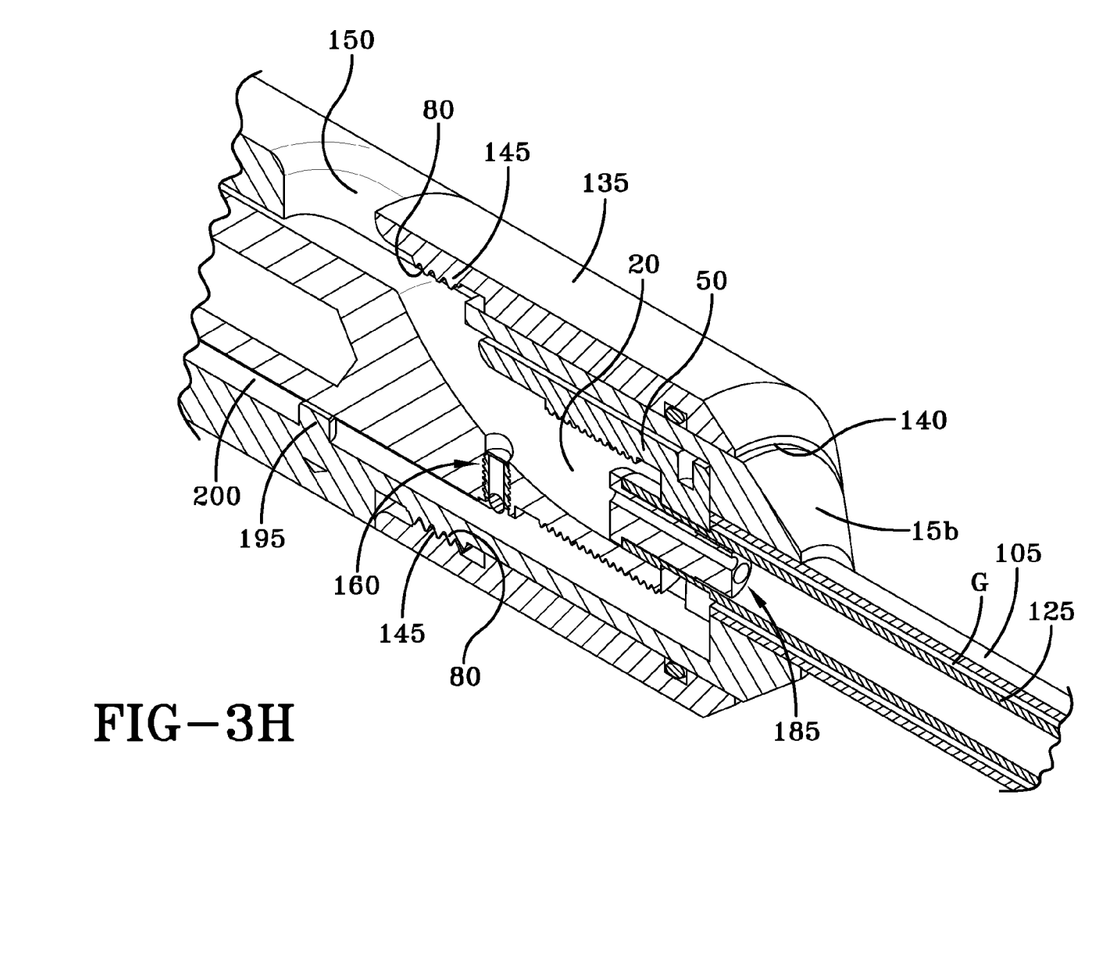
FIG. 3H is an isometric cross-sectional view of the assembly of FIG. 3G.

In order to prevent an unintended rotation of the retention collar receiver 20 during rotation of the retention collar 50, an anti-rotation element 195 may extend inward from the interior wall of the actuator housing 15b and engage the retention collar receiver (see FIGS. 3D and 3H). The retention collar receiver 20 is provided with a longitudinally directed slot 200 that receives the anti-rotation element 195. With the anti-rotation element 195 protruding into the slot 200, the retention collar receiver is permitted to reciprocate linearly within the housing 15, but is substantially prevented from rotating.

Referring again to FIGS. 3B and 3D, it can also be observed that the centerlines of the slot 40 in the connecting end 15b of the actuator housing 15 and the slot 55 in the rotatable retention collar 50 are aligned such that when the probe tube 105 is engaged with the actuator housing slot 40 and the sample capture element is engaged with the retention collar slot 55 and retention rib 60, the sample capture element is automatically concentrically arranged within the probe tube with a gap G therebetween. Therefore, the coupling system 5 not only securely and efficiently couples the sample capture element 125 to the actuator 10, it also ensures that the sample capture element can reciprocate within the probe tube 105 without contacting interference therewith. Without this concentric location, undesirable wear would likely result, including wear at both the shoulder and groove areas of the sample capture element 125 if the sample capture element were to move at an angle to the probe tube 105.

As illustrated in FIG. 3D, the coupling system 5 may also include a retention collar position maintenance feature 160. This position maintenance feature 160 may be used to ensure that the retention collar remains in an unlocked and/or locked position unless deliberately moved therefrom. In this case, the position maintenance feature 160 includes a ball 165 that protrudes from a bore 170 in the retention collar receiver 20 to ride against an inside face of the retention collar 50. The ball 165 is biased toward the retention collar 50 by a spring 175 that resides in the bore 170. The retention collar 50 may be provided with one or more detent notches 180 that engage the spring-loaded ball 165 to resist inadvertent rotation of the retention collar.

As depicted in FIG. 3E, with the probe tube 105 engaged with the actuator housing connecting end 15b and the sample capture element 125 securely coupled to the retention collar receiver 20, the cover plate 35 may be installed to the mating integral half 30 of the actuator housing connecting end 15b. The cover plate 35 may be at least partially positioned and retained on the integral half 30 of the actuator housing connecting end 15b by the retaining pins 45.

Referring now to FIGS. 3F-3H, it can be observed that the cover plate 35 is retained on the integral half 30 of the actuator housing connecting end 15b by an end cap 135 that slips over the probe tube 105. A distal end 135b of the end cap 135 includes a central bore 140 through which a portion of the actuator housing connecting end 15b passes. In this particular embodiment, the end cap 135 is releasably affixed to the actuator housing 15 by threaded engagement therewith. To this end, the actuator housing 15 includes external threads 80 near a proximal end of the actuator housing connecting end 15b, and the end cap 135 is provided with corresponding internal threads 145 near its proximal end 135a such that the end cap may be threaded onto and secured to the actuator housing 15 as shown in FIG. 3E.

As is apparent from the drawing figures, the integral actuator housing connecting end 15b and its externally threaded portion may be of reduced size (e.g., diameter) to allow for the use of an end cap 135 having an exterior dimension that approximates the exterior dimension of the remainder (or adjoining portion) of the actuator housing 15. Alternatively, the integral actuator housing connecting end 15b and/or its externally threaded portion may be of a larger exterior dimension (e.g., the same dimension as the remainder or adjoining portion of the actuator housing), in which case the end cap 135 may have an exterior dimension that is greater than the remainder or adjoining portion of the actuator housing 15.

As shown in the drawing figures, an opening 150 may be formed through the actuator housing 15 to permit the passage therethrough of material supply/return lines 155. Such supply/return lines 155 may be connected to corresponding ports in the proximal end of the sample capture element 125, as described in more detail in U.S. patent application Ser. No. 12/823,655 referenced above. As shown herein, a plug 185 (strain relief) having supply/return line connection ports may be located in the proximal end 125a of the sample capture element 125 for this purpose.

Figure 2:
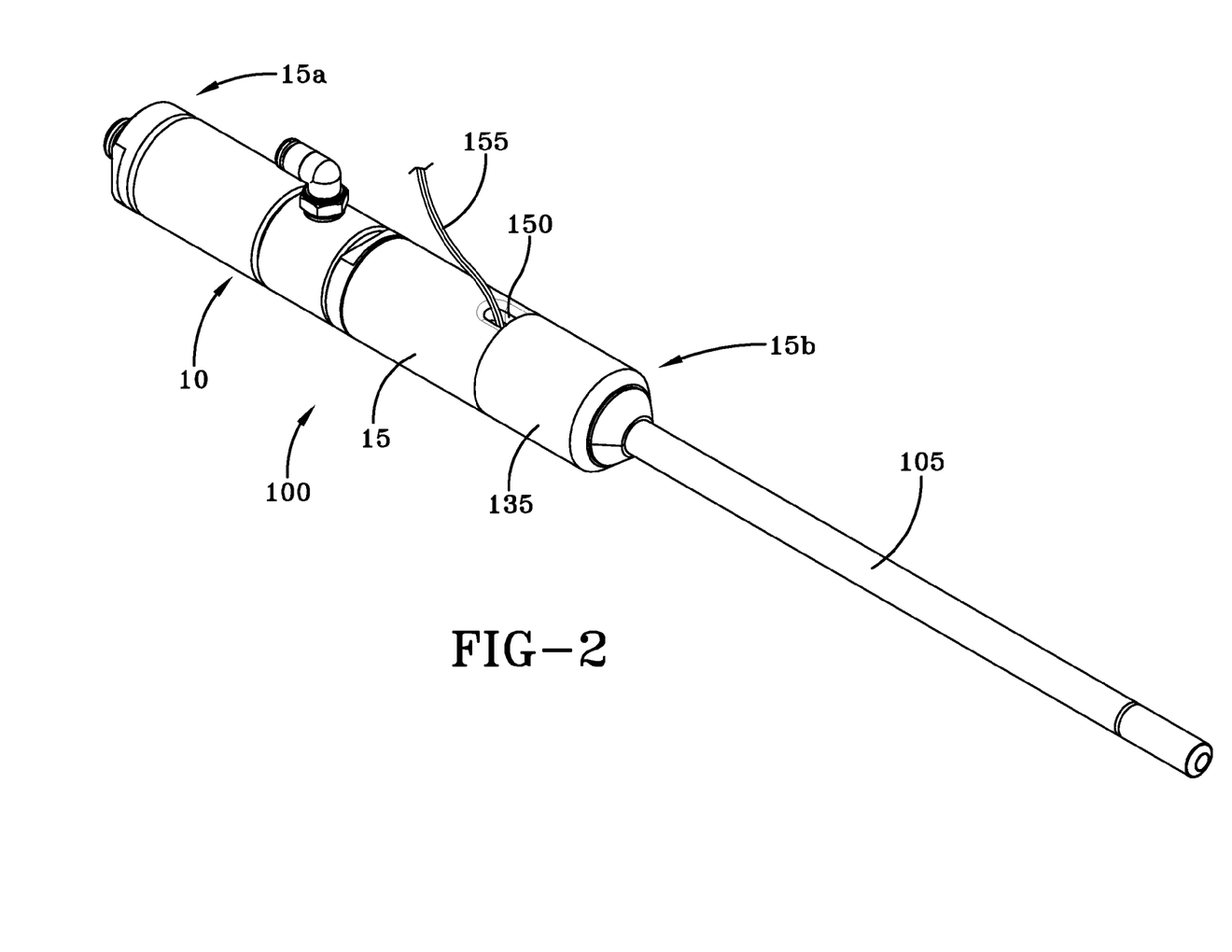
FIG. 2 is an assembled view of the sample capture device of FIG. 1.

The disassembled sample capture device 100 of FIG. 1 may be placed in the assembled state of FIG. 2 as shown by FIGS. 3A-3H. Disassembly may be accomplished in reverse order. Obviously, the coupling/decoupling of an extendable element to/from an actuator according to the present invention may differ to some extent from the process shown and described herein depending on the specific actuator and extendable element involved.

Therefore, it should be apparent that while certain embodiments of the present invention are described in detail above, the scope of the invention is not to be considered limited by such disclosure, and modifications are possible without departing from the spirit of the invention as evidenced by the following claims:

What is claimed is:

1. A system for coupling an extendable element to an actuator, comprising:
    an actuator housing containing an actuator, said actuator housing having an integral distal connecting end, said integral connecting end having a cross-sectional shape that terminates in a cover plate mating face defined by a plane that runs substantially parallel to the longitudinal centerline of the actuator housing;
    an opening in a distal end of said integral connecting end of said actuator housing, said opening allowing passage of an extendable element therethrough;
    a cavity in said integral connecting end of said actuator housing;
    a rotatable collar located within said cavity, said rotatable collar adapted for rotation about one end of an extendable element so as to couple said extendable element to a motive element of said actuator;
    a cover plate of a size and shape that compliments said integral connecting end of said actuator housing, said cover plate having an opening in its distal end for allowing passage of an extendable element therethrough, said cover plate adapted to mate with said cover plate mating face of said integral connecting end of said actuator housing to enclose said rotatable collar and a portion of an extendable element; and
    a substantially hollow end cap for enclosing said integral connecting end of said actuator housing and said cover plate, a proximal end of said end cap releasably attached to said actuator housing, a distal end of said end cap having a hole for passage therethrough of an extendable element.

2. The system of claim 1, wherein said actuator is a linear actuator having a reciprocatable piston.

3. The system of claim 2, wherein a retention collar receiver portion of said piston extends into said cavity in said distal connecting end of said actuator housing.

4. The system of claim 3, wherein at least a section of said retention collar receiver that extends into said cavity in said distal connecting end of said actuator housing is externally threaded, and a mating portion of said rotatable collar is internally like-threaded, such that said collar is in threaded engagement with said retention collar receiver during rotation of said collar.

5. The system of claim 1, wherein said rotatable collar includes a slot for receiving an end portion of an extendable element, said slot being of a stepped configuration so as to form a rib at a distal end of said collar, said rib for engaging a corresponding groove in an extendable element to be coupled to said actuator.

6. The system of claim 1, further comprising an outer tube within which an extendable element may reciprocate when connected to said actuator, said outer tube sized to pass through said openings in said integral connecting end of said actuator housing and said cover plate and connectable to said integral connecting end of said actuator housing.

7. The system of claim 6, further comprising at least one pin extending from said cover plate mating face, said at least one pin located adjacent said opening in said distal end of said integral connecting end of said actuator housing to engage at least one corresponding retention groove located in an exterior of said outer tube.

8. The system of claim 1, further comprising external threads on said actuator housing and mating internal threads on said end cap for providing releasable attachment of said end cap to said actuator housing.

9. The system of claim 1, wherein one or more rotation tool holes are present on an exterior surface of said rotatable collar in to facilitate rotation of said collar with a tool.

10. The system of claim 1, wherein said actuator housing further includes an opening that leads from an exterior thereof into said cavity.

11. The system of claim 1, wherein said actuator is selected from the group consisting of a pneumatic actuator, a hydraulic actuator, and an electric actuator.

12. A system for coupling an extendable sample capture element to an actuator portion of a sample capture device, said sample capture element of said sample capture device reciprocatably located within an outer probe tube, said system comprising:
    an actuator housing containing an actuator, said actuator housing having an integral distal connecting end, said integral connecting end having a cross-sectional shape that terminates in a cover plate mating face defined by a plane that runs substantially parallel to the longitudinal centerline of the actuator housing;
    an opening in a distal end of said integral connecting end of said actuator housing, said opening adapted to receive a portion of a proximal end of said probe tube therein;
    a cavity in said integral connecting end of said actuator housing;
    a rotatable collar located within said cavity, said rotatable collar adapted for rotation about a proximal end of said sample capture element that extends from said proximal end of said probe tube, so as to couple said sample capture element to a motive element of said actuator;
    a cover plate of a size and shape that compliments said integral connecting end of said actuator housing, said cover plate having an opening in its distal end for a receiving a portion of a proximal end of said probe tube therein, said cover plate adapted to mate with said cover plate mating face of said integral connecting end of said actuator housing to enclose said rotatable collar and a received portion of said probe tube; and
    a substantially hollow end cap for enclosing said integral connecting end of said actuator housing and said cover plate, a proximal end of said end cap releasably attached to said actuator housing, a distal end of said end cap having a hole for passage therethrough of said probe tube.

13. The system of claim 12, wherein said actuator is a linear actuator having a reciprocatable piston.

14. The system of claim 13, wherein a retention collar receiver portion of said piston extends into said cavity in said distal connecting end of said actuator housing.

15. The system of claim 14, wherein at least a section of said retention collar receiver that extends into said cavity in said distal connecting end of said actuator housing is externally threaded, and a mating portion of said rotatable collar is internally like-threaded, such that said collar is in threaded engagement with said retention collar receiver during rotation of said collar.

16. The system of claim 12, wherein said rotatable collar includes a slot for receiving said proximal end of said sample capture element, said slot being of a stepped configuration so as to form a rib at a distal end of said collar, said rib for engaging a corresponding groove in said sample capture element.

17. The system of claim 12, further comprising external threads on said actuator housing and mating internal threads on said end cap for providing releasable attachment of said end cap to said actuator housing.

18. The system of claim 12, wherein one or more rotation tool holes are present on an exterior surface of said rotatable collar in to facilitate rotation of said collar with a tool.

19. The system of claim 12, wherein said actuator housing further includes an opening that leads from an exterior thereof into said cavity, said opening for permitting passage of material supply/return lines connected said proximal end of said sample capture element.

20. A method for coupling an extendable element to an actuator, comprising:
    providing an actuator housing containing an actuator, said actuator housing having an integral distal connecting end, said integral connecting end having a cross-sectional shape that terminates in a cover plate mating face defined by a plane that runs substantially parallel to the longitudinal centerline of the actuator housing;
    passing a coupling end of an extendable element through an opening provided in a distal end of said integral connecting end of said actuator housing and into a cavity in said integral connecting end of said actuator housing;
    rotating a rotatable retention collar located within said cavity about said coupling end of said extendable element, said rotatable retention collar connected to a motive element of said actuator by a retention collar receiver such that said retention collar also couples said extendable element to said actuator;
    mating a cover plate to said cover plate mating face of said integral connecting end of said actuator housing to enclose said rotatable collar and a portion of an extendable element, said cover plate of a size and shape that compliments said integral connecting end of said actuator housing and having an opening in its distal end for allowing passage of said extendable element therethrough; and
    passing a substantially hollow end cap over said extendable element, said integral connecting end of said actuator housing and said cover plate, and releasably attaching said end cap to said actuator housing so as to enclose said integral connecting end of said actuator housing and said cover plate.

* * * * *